United States Patent [19]

Pallas et al.

[11] Patent Number: 5,707,551
[45] Date of Patent: Jan. 13, 1998

[54] NONAQUEOUS SUSPENSION CONCENTRATES OF HIGHLY WATER-SOLUBLE SOLIDS

[75] Inventors: Norman Robert Pallas, Freehold; James Lyle Hazen, Plainsboro; Robert Jene Riedemann, Neptune, all of N.J.

[73] Assignee: Rhone-Poulenc Inc., Cranbury, N.J.

[21] Appl. No.: 362,057

[22] Filed: Dec. 22, 1994

[51] Int. Cl.⁶ .................................................. B01J 13/00
[52] U.S. Cl. ........................... 252/308; 71/64.08; 137/13; 241/16; 252/309; 252/314; 252/353; 252/363.5
[58] Field of Search ..................... 252/308, 309, 252/314, 353, 363.5, 559, DIG. 2, DIG. 14; 137/13; 241/16; 510/418, 421, 427

[56] References Cited

U.S. PATENT DOCUMENTS

| | | | |
|---|---|---|---|
| 2,920,045 | 1/1960 | Hearn et al. | 252/526 |
| 3,089,848 | 5/1963 | Morway | 252/18 |
| 3,882,247 | 5/1975 | Bullock | 424/337 |
| 3,960,742 | 6/1976 | Leonard | 252/559 X |
| 3,984,463 | 10/1976 | Pilgram | 260/501.17 |
| 4,183,741 | 1/1980 | West et al. | 71/92 |
| 4,227,911 | 10/1980 | Leonard et al. | 71/77 |
| 4,265,406 | 5/1981 | Palgrave et al. | 241/16 |
| 4,294,633 | 10/1981 | Clay | 149/2 |
| 4,331,490 | 5/1982 | Palgrave et al. | 149/46 |
| 4,372,777 | 2/1983 | Le Clair et al. | 71/93 |
| 4,393,151 | 7/1983 | Dawans et al. | 253/363.5 X |
| 4,482,372 | 11/1984 | Palgrave et al. | 71/35 |
| 4,673,526 | 6/1987 | Zabotto et al. | 252/DIG. 14 |
| 4,784,788 | 11/1988 | Lancz | 252/DIG. 14 |
| 4,824,475 | 4/1989 | Markley et al. | 71/93 |
| 4,876,354 | 10/1989 | Siegel et al. | 548/341 |
| 4,918,085 | 4/1990 | D'Silva et al. | 514/407 |
| 4,943,307 | 7/1990 | Detre et al. | 71/3 |
| 4,950,424 | 8/1990 | Van der Hoeven et al. | 252/559 X |
| 5,079,370 | 1/1992 | D'Silva et al. | 548/365 |
| 5,082,591 | 1/1992 | Marchetto et al. | 252/353 X |
| 5,179,096 | 1/1993 | Gentilini et al. | 514/253 |
| 5,223,524 | 6/1993 | Valcke | 514/383 |
| 5,468,418 | 11/1995 | Rabone | 252/DIG. 14 |

*Primary Examiner*—Richard D. Lovering
*Attorney, Agent, or Firm*—John A. Shedden

[57] ABSTRACT

Stable, concentrated nonaqueous suspensions of water-soluble solids are prepared by using water-miscible organic liquid carriers, preferably lower alkadiols in conjunction with a specific three component surfactant system, i.e., a system comprising a nonionic polymeric viscosity improver surfactant; an anionic surfactant; and a nonionic surfactant having a bulky hydrophobic substituent group.

5 Claims, 2 Drawing Sheets

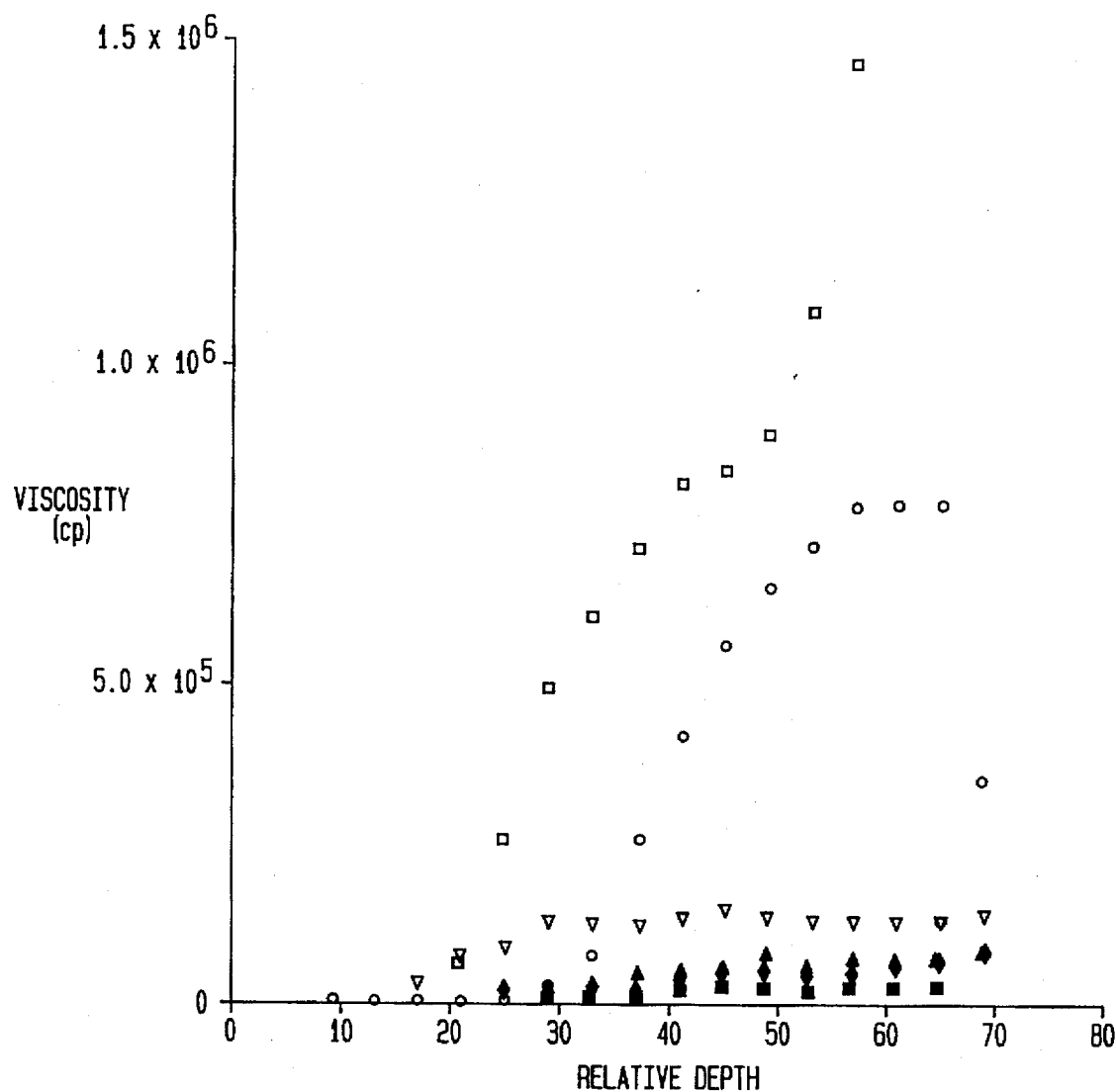

NONAQUEOUS SUSPENSION CONCENTRATES OF HIGHLY WATER-SOLUBLE SOLIDS

BACKGROUND OF THE INVENTION

1. Field of the Invention

The present invention relates to a method for preparing concentrated suspensions of water-soluble solids with excellent storage stability and the concentrates thus formed. The method comprises suspending the solids in a water-soluble organic liquid such as a low molar mass glycol in the presence of a three component surfactant system.

2. Description of the Art

Many handling problems may arise when one is forced to prepare aqueous end-use formulations and/or slurries from solids, especially active solids, e.g. wettable bioactive powders as is often the situation in the agricultural industry. Farmers preparing tank mixes of herbicides, insecticides and/or other bioactives from solids for applications to crop and soil are exposed to certain safety hazards and inconveniences due to the generation of noxious dusts which may be irritable to the skin and hazardous to breathe. Additionally, finely ground powders, even so-called wettable powders, of many water-soluble bioactives when prepared as tank mixes do not disperse well; have poor spontaneity of "bloom"; have low suspensibility, have poor redispersibility and are incompatible with other bioactives as compared to liquid bioactive concentrates. Thus, final formulators, such as farmers, when preparing diluted aqueous active compositions find that the handling and application of solids materials such as fertilizers, are much facilitated if the material can be supplied in a fluid rather than solid form. Economics then dictates that the active material be supplied in a highly concentrated fluid to the final formulator. Saturation solubility in water of many water-soluble active constituents, such as potassium chloride, is too low to make it economical to supply it to the end-user simply in the form of a solution. Alternatively, highly concentrated suspensions of water soluble compounds, both in water and in organic liquids, have very poor storage; freeze/thaw; and heat/cool stability. As a result of the spontaneous crystal dissolution-recrystallization process, there occurs a progressive increase in the size of the particulate active material. This increase in particle size results in settling, bleed and changes in visco-elastic properties and thus severely limits concentrate loading levels.

The instant invention concerns a unique formulation which, to a great extent, addresses and overcomes the above problems.

Particle size stability of water-soluble particulate solids is obtained in a twofold manner. Firstly, by appropriate selection of the organic carrier used as the continuous phase, the temperature coefficient of solubility can be controlled, thus stabilizing particle size of the solids throughout usual commercial storage times and temperature cycles. The major component of the carrier liquid is nonaqueous, though small amounts of water may be used to modify the performance. Secondly, recognizing that a small number of large particles has a smaller total surface area than a large number of small particles regardless of morphology, the surface-free energy of the active solid material is lowered via surfactant adsorption on the particle surface, thus reducing the drive to obtain a minimization of the surface area which promotes growth of the particles.

The particle size stability and other desirable characteristics of the concentrate such as low viscosity, minimum syneresis and high bloom are primarily controlled through the use of a three component surfactant system.

The first component, a nonionic viscosity-improver material, preferably a polymeric material and most preferably an ethylene oxide-propylene oxide block copolymer, is primarily used, through rheology control, to create a stable dispersion and secondarily to mollify crystal growth.

The second component, an anionic surfactant, preferably a sulfonate, albeit having a syneresis-increasing influence, is utilized primarily to synergistically reduce the viscosity enhancing effect of the polymeric first component and secondarily, as a result of its affinity for the surface of the solids, to aid in the dispersibility of the solids particles.

The third component, which is a bulky nonionic surfactant containing a large hydrophobic group, preferably an ethoxylated tristyryl phenol, is primarily used to reduce packing of the particles, i.e. reduce syneresis or settling and serendipitiously to enhance the bloom or dispersibility that occurs when the concentrate composition is diluted by pouring it into an aqueous medium to achieve the final formulation end-use concentration.

This third component also has a tendency to increase the viscosity of the concentrate.

Optionally, a minor amount of water may be added to the concentrate primarily to assist in adjusting the temperature coefficient of solubility which ultimately minimizes changes in particle size.

Palgrave, et al. (U.S. Pat. No. 4,265,406) disclose the use of an additive such as a polysaccharide to at least partially inhibit regrowth at crystal surfaces when comminuting concentrated solid material such as water soluble explosive or fertilizer salts in saturated solutions.

Through use of the organic carrier and surfactant systems of this invention, exceptionally high loadings, i.e. from about 40 to 85% by weight of total composition, of suspensions of water-soluble solids are prepared which exhibit minimal changes in particle size and are characterized by settling and visco-elastic properties that realize suspensions which are extremely stable even under long term storage conditions.

BRIEF DESCRIPTION OF DRAWINGS

FIG. 2 is a graph of the results of the Heliopath viscosity evaluations of the ammonium dihydrogen phosphate Examples 26–33.

DETAILED DESCRIPTION OF THE INVENTION

Figure 1:
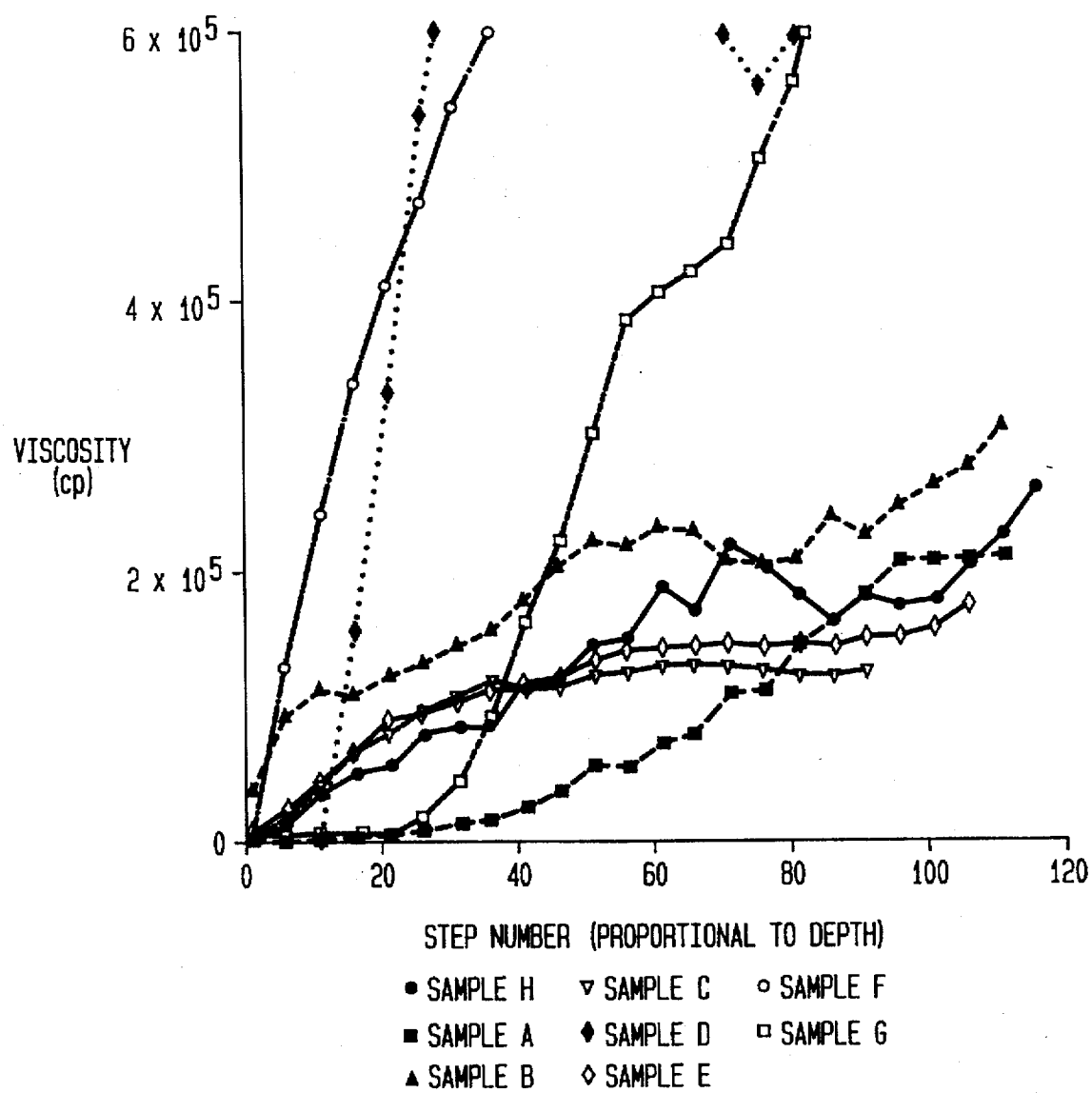
FIG. 1 is a graph of the results of the Heliopath viscosity evaluations of the potassium nitrate Examples 18–25.

The formulations of the instant invention are eminently suitable for suspending solids essentially of any water-soluble materials that, at the loading being considered in the concentrate, exist as a separate solid phase in the fully formulated concentrate. Many such materials find application in the explosive and agricultural areas, especially in the fertilizer fields. Examples of such water-soluble materials include salts such as potassium nitrate, ammonium dihydrogen phosphate, ammonium nitrate, sodium nitrate, calcium nitrate, potassium chloride, sodium chloride, ammonium phosphate, ammonium polyphosphate, potassium hydrogen phosphate, disodium hydrogen phosphate and the like, and non-salt-like compounds such as urea.

By the term "water-soluble" is meant any material having a solubility in water of greater than one (1) weight percent based on the total weight of the material and the water at 24° C.

The concentration or loading of the solid material in the formulations of this invention can be from 40 to 85 weight percent; preferably from 50–80 weight percent; and most preferably from 55–70 weight percent based on the total weight of the concentrate.

The volume average diameter particle size of the water-soluble solid material can be from 0.5 to 500 microns; preferably from 30 to 200 microns; most preferably from about 80 to about 120 microns.

The carrier can be any water-miscible low molecular weight organic fluid which is liquid at room temperature. The term "water-miscible" means that the organic liquids are miscible with water in all proportions, i.e. will form a single phase with the water.

Where the water-soluble solids are bioactive, it is preferred that the carrier be inert or at least acceptable for the intended end-use of the diluted concentrate. For example, if the solids are pesticidally active, the carrier should be agronomically acceptable.

All water-miscible organic liquid carriers do not work with equal effectiveness and it is generally preferred that the organic liquid have hydroxide functionality and relatively low molecular weight; thus mono- or poly functionality lower alcohols are particularly effective together with their ethers or esters. Among these are the lower alkanols and alkadiols. Maximum water miscibility is obtained with $C_1$–$C_4$ alcohols (methanol, ethanol, isopropyl alcohol, etc.). Of the glycols (alkadiols, alkatriols, etc., e.g., ethylene glycol and propylene glycol) diethylene glycol are particularly preferred.

The carriers of this invention also include water-miscible ketones, such as acetone, methyl ethyl ketone, methyl isobutyl ketone and cyclohexanone; and ethers. Water-soluble or strongly polar solvents such as formamide, dimethyl formamide, dimethyl sulfoxide, or N-methyl pyrrolidone and the like are acceptable. Partially miscible liquids such as furfural and furfuryl alcohol are also useful as carriers in this invention. Mixtures of different liquids are often suitable.

The carrier concentration in the suspension concentrate should be from 11 to 58 weight percent based on the total weight of the concentrate; preferably from 20 to 45 weight percent, most preferably from 22 to 35 weight percent.

The stabilization zone properties of the concentrated water-soluble solids/carrier compositions are achieved primarily through the use of a three component surfactant system which is from 4 to 15 weight percent of the total weight of the concentrate.

The first component, which is a nonionic viscosity-improver material, preferably a polymeric material with a volume mass of less than 15,000, is used to control the rheology of the concentrate and thereby to primarily create a stable dispersion and secondarily to mollify the crystal growth of the solids particles.

Examples of acceptable nonionic viscosity improvers are the polyacrylic acids and their sodium salts; the polyglycol ethers of fatty alcohols and polyethylene oxide or polypropylene oxide condensation products; and mixtures thereof and include ethoxylated alkyl phenols (also designated in the art as alkylaryl polyether alcohols); ethoxylated aliphatic alcohols (or alkyl polyether alcohols); ethoxylated fatty acids (or polyoxyethylene fatty acid esters); ethoxylated anhydrosorbitol esters (or polyethylene sorbitan fatty acid esters), long chain amine and cyclic amine oxides which are nonionic in basic solutions; long chain tertiary phosphine oxides; and long chain dialkyl sulfoxides.

Preferably the nonionic viscosity improvers are polymeric such as ethoxylated polyoxypropylene glycols (polyalkylene oxide block copolymers): ethoxylated polyoxypropylene monohydric alcohols (polyalkylene oxide blocks copolymers of monohydric alcohols); and ethoxylated polyoxypropylene alkyl phenols (polyalkylene oxide block copolymers of alkyl phenols).

Most preferably the viscosity improvers are ethylene oxide-propylene oxide block copolymers of the formula:

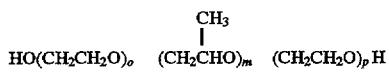

wherein o and p are moles of ethylene oxide; in the range wherein o is from 2 to 128 and p is from 2 to 128 and m is moles of propylene oxide in the range of from 16 to 67.

The viscosity improver is present in the concentrate at from 2 to 20 weight percent; preferably from 2 to 7 weight percent; and most preferably from 2 to 6 weight percent; said percentage based on the total weight of the concentrate.

The second component of the surfactant stabilizer system is an anionic surfactant whose primary function is to synergistically control the viscosity increase caused by the crystal growth inhibiting first component. Secondarily, its affinity for adhesion to the surface of the particulate solids aids in the dispersibility of the particles.

Anionic surfactants useful herein include alkyl and alkyl ether sulfates. These materials have the respective formulae $ROSO_3M$ and $RO(C_2H_4O)_x SO_3M$ wherein R is an alkyl, alkenyl or alkylaryl group of about 8 to about 22 carbon atoms, x is 1 to 10, preferably 1 to 4, and M is a water-soluble cation such as ammonium, sodium, potassium, magnesium, triethanolamine (TEA), etc. The alkyl ether sulfates useful in the present invention are condensation products of ethylene oxide and monohydric alcohols having about 8 to about 22 carbon atoms. Specific examples of the above sulfates include ammonium lauryl sulfate, magnesium lauryl sulfate, sodium 2-ethyl-hexyl sulfate, sodium octyl sulfate, sodium oleyl sulfate, sodium tridecyl sulfate, triethanolamine lauryl sulfate, ammonium linear alcohol, ether sulfate ammonium nonylphenol ether sulfate, and ammonium monoxynol-4-sulfate.

Another suitable class of anionic surfactants are the water-soluble salts of the general formula:

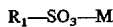

wherein $R_1$ is selected from the group consisting of:

i) a straight or branched chain, saturated aliphatic hydrocarbon radical having from 8 to 24, preferably 12 to 18 carbon atoms;

ii) a mono-, di-, or tri- $C_1$–$C_6$ alkyl substituted aryl wherein the aryl is preferably a phenyl or naphthyl group;

iii) alpha-olefins having 12 to 24 carbon atoms, preferably 14 to 16 straight chain carbon atoms, most preferably 1-dodecene, 1-tetradecene, 1-hexadecene, 1-octadecene, 1-eicosene, and 1-tetracosene; and iv) napthalene-formaldehyde condensation products.

Additional examples of anionic synthetic surfactants which come within the terms of the present invention are: i) the isethionates, i.e. the reaction products of fatty acids esterified with isethionic acid and neutralized with sodium hydroxide where, for example, the fatty acids are derived from coconut oil; and ii) the n-methyl taurates, i.e., the sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic synthetic surfactants include the classes designated as the sulfosuccinates and sulfo succinamates. These are of the general formulae:

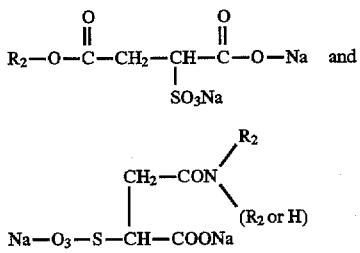

respectively, wherein $R_2$ is a $C_2$–$C_{10}$ alkyl or alkylamido. These classes include such surface active agents as disodium N-octadecylsulfo-succinamate; tetrasodium N-(1,2-dicharbxyethyl)-N-octadecylsulfo-succinamate; diamyl ester of sodium sulfosuccinic acid; dihexyl ester of sodium sulfosuccinic acid; and dioctyl esters of sodium sulfosuccinic acid.

Another class of anionic organic surfactants are the B-alkyloxy alkane sulfonates. These compounds have the following formula:

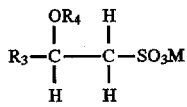

where $R_3$ is a straight chain alkyl group having from 6 to 20 carbon atoms, $R_4$ is a lower alkyl group having from 1 to 3 carbon atoms, and M is a water-soluble cation as hereinbefore described.

Specific examples of B-alkyloxy-alkane-1-sulfonates, or alternatively 2-alkyloxy-alkane-1-sulfonates include:

potassium-B-methoxydecanesulfonate, sodium 2-methoxytridecanesulfonate, potassium 2-ethoxytetradecylsulfonate, sodium 2-isopropoxyhexadecylsulfonate, lithium 2-t-butoxytetradecylsulfonate, sodium B-methoxyoctadecylsulfonate, and ammonium B-n-propoxydodecylsulfonate.

Also to be included in the anionic class of surfactants are the disulfonates of the general formula:

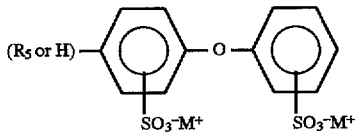

wherein $R_5$ is a $C_8$–$C_{20}$ alkyl group and M is a water-soluble cation as hereinabove described. The preferred anionics of the disulfonate class are disodium dodecyl diphenyloxide disulfonate and ethoxylated nonylphenyl ammonium disulfonate. All of the above-described anionic surfactants and mixtures thereof may or may not be ethoxylated with from about 1 to about 10 ethylene oxide units per "R" unit.

The anionic surfactant is present in the concentrate at from 1 to 20 weight percent; preferably from 1 to 7 weight percent; and most preferably from 1 to 5 weight percent; said percentage based on the total weight of the concentrate.

The third component of the surfactant stabilizer system is a bulky nonionic surfactant containing a large hydrophobic group. These third components are of the formula $R_6O(C_nH_{2n}O)_x R_7$ wherein R6 is selected from the group consisting of a phenyl; a mono-, di- or tri-substituted phenyl; a phenyl $C_1$–$C_6$ alkyl; and a mono-, di-, or tri-substituted phenyl $C_1$–$C_6$ alkyl wherein the phenyl substituent group(s) each have a total of 1 to 30 carbon atoms, and wherein each substitution can be a saturated or unsaturated straight or branched carbon chain, a phenyl, an alkyl phenyl, a phenyl alkyl, or an alkyl phenyl alkyl group; wherein n is from 2 to 4 and may be the same or different for each alkylene oxide unit; wherein $R_7$ is a hydrogen, phosphate or sulfate entity; and wherein X is from 2 to 100. Preferably this component is a dinonyl phenol or a tristyrylphenol, most preferably an ethoxylated dinonyl phenol or tristyrylphenol and/or any esters thereof. These ethoxylated tristyrylphenols and their derivatives can be described as comprising at least one poly-oxy ethylenated and/or -oxy propylenated poly (1-pheny ethyl) phenol or phenyl ester of the formula:

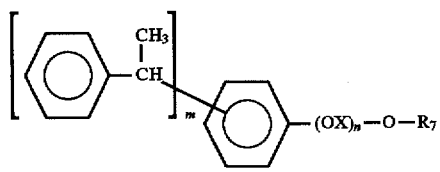

wherein:

m is 2 or 3;

(OX) is a recurring oxy ethylenated and/or oxy propylenated unit;

n is from 12 to 35; preferably from 16 to 30; and $R_7$ is a hydrogen, phosphate or sulfate entity.

The bulky nonionic surfactant is present in the concentrate at from 1 to 20 weight percent; preferably from 1 to 7 weight percent; and most preferably from 1 to 5 weight percent; said percentage based on the total weight of the concentrate.

Water can optionally be added to the concentrate at from 0 to 30 weight percent. The water acts primarily to control the temperature coefficient of solubility and thus helps to minimize particle size changes. Preferably, the water is added at from 0 to 20 weight percent; and most preferably from about 1 to 8 weight percent; said water percentages being based on the total weight of the concentrate.

Although the method of preparing the concentrates of this invention is not critical, a preferred approach is to first prepare a mixture of the nonionic surfactant with the bulky hydrophobic group; the anionic surfactant; the organic liquid carrier; and the water (if any) and load this mixture into a mill or grinder such as an "Eiger" mill. The nonionic polymeric viscosity improver is then milled into the mixture. The solid water-soluble material that is to be concentrated in suspension is added last and milled until the desired particle size and distribution is obtained. The particle size should not be so fine that the initial (24 hour) viscosity exceeds 30,000 cps at room temperature. Although the volume average diameter particle size of the water-soluble solid material can be from about 0.5 microns to about 500 microns, preferably from about 30 to about 200 microns, it is most preferably from about 80 microns to about 120 microns.

To determine the stability of the concentrates of this invention, a storage stability program is conducted on numerous suspension concentrate samples over time. The samples are initially measured for viscosity and syneresis after 24 hours. Duplicate samples are then placed in storage at room temperature (about 24° C.) and 50° C. for 2, 3 and 4 week evaluations. Percent syneresis and a vertical "T-bar" viscosity profiles are measured at each interval. Pourability is tested at three or four weeks.

The viscosity measurements were made using a Brookfield Rheometer (Model DV III) and a Brookfield LV spindle set. The viscometer was run for 120 seconds at each selected speed; the readings were recorded every ten seconds; and the twelve digital readings averaged. Initial viscosities are measured at 24 hours, plus or minus 4 hours, preferably ±2 hours. An acceptable initial viscosity range at room temperature is from about 100 to 30,000 cps.

The vertical viscosity profile is conducted on each sample using a Brookfield Heliopath T-bar spindle set, with the tips cut off, at 12 rpm or less. The container is a two ounce jar having a diameter of four centimeters and a height of eight centimeters. The vertical profile is run from the surface of the liquid to the bottom and a scale is set from 0 to 100 representing the depth of the liquid.

A suspension is within the invention if after two weeks from initial preparation and at room temperature (24° C.), the Heliopath viscosity, at two inches below the surface of the concentrate, does not exceed 400,000 cps.

After the viscosity profile is completed, a small glass rod is carefully submerged to the bottom center of the jar. The resistance of the glass rod in penetrating through the sample is subjectively evaluated for the degree of compacting. Any caking or claying is detected by simply inverting the sample container and noting the presence of material which does not come off the bottom of the container within thirty (30) seconds.

The syneresis is determined by measuring the respective depths in the eight ounce sample jar of the type used in the Heliopath viscosity measurements. The liquid is measured in millimeters with a ruler from the bottom of the liquid to the top surface. The top layer separation (if any) is also measured and that layer is calculated as a percentage of the total sample height. An acceptable result is realized if the percent syneresis is equal to or less than thirty (30) percent after twenty-four (24) hours storage at 24° C. and thereafter less than five percent is visible after thirty (30) inversions.

The pourability is quantitatively determined utilizing a Bostwick Consistometer No. 24925-00. Approximately fifty (50) milliliters of concentrate at 24° C. are put into the Consistometer apparatus. The gate is opened while simultaneously starting a stop watch. The amount of time needed for the material to reach the 10 centimeter mark is noted or the time at which the material stops flowing is noted: whichever occurs first. An acceptable result is obtained if the material reaches the 10 cm mark at, or in less than, one minute.

The pourability is qualitatively determined by utilizing the aforementioned eight ounce sample jar; turning it upside down; and observing the suspension's movement. The flow is subjectively determined to be "difficult" if high gloppiness appears; "moderately difficult" if ketchup-like in flow; "slightly difficult" if a creamy salad-dressing type of flow; and "easy" if it flows like a thin, latex paint.

The particle size is measured using a Galai Instruments Particle Size Analyzer Model CIS-100 and following the manufacturer's instructions. Measurements are made before the storage tests begin and after they are finished. An acceptable result is obtained if the particle size does not change by more than fifty (50) percent by the end of the four week storage tests. Typically, less than twenty (20) percent increase in particle size is found after three weeks storage or after three freeze/thaw cycles using the concentrate suspensions of this invention.

The processes of the present invention are demonstrated in detail in the following non-limiting working examples wherein all parts and percentages are by weight unless otherwise indicated.

EXAMPLE I

A mixture of 3.3 weight percent tristyrylphenol (16) ethoxylate (Soprophor BSU, a trademark for a bulky nonionic surfactant of Rhone-Poulenc); 3.3 weight percent ethoxylated-propoxylated block copolymer (Antarox F-88, a (97 EO 39 PO 97 EO) polymeric viscosity improver trademark of Rhone-Poulenc); 3.3 weight percent RHODACAL DSB which is the trademark of Rhone-Poulenc for a 50% water/50% disodium dodecyl diphenyloxide disulfonate anionic surfactant mixture; and 25 weight percent diethylene glycol (reagent grade) is milled in an Eiger mill to effect a uniform blend. Sixty five weight percent potassium nitrate (fertilizer grade) is then added to the mixture and milled until essentially all particles are less than 600 microns volume mean diameter and at least 85% are between 50 microns and 600 microns. This batch is identified as the "Coarse" grind. All weight percentages are based on the total weight of the mixture concentrate. The above procedures are carried out with a second mix of the material and milled until essentially all particles are less than 600 microns volume mean diameter and at least 35% of the material has a volume mean diameter of less than 50 microns. This batch is identified as the "Fine" grind.

The above prepared batches of 65% potassium nitrate, 25% diethylene glycol and 10% surfactant system (plus water) are designated samples A-1C and A-1F respectively. Two other samples are similarly prepared. In the first, the total surfactant (plus water) level is reduced to 7 weight percent by utilizing only 2.3 weight percent tristyrylphenol ethoxylate; 1.2 weight percent disodium dodecyl diphenyloxide disulfonate; 1.2 weight percent water; and 2.3 weight percent of the ethoxylated-propoxylated block copolymer. The diethylene glycol is increased to 28 weight percent to make up the difference. These batches, i.e., the Coarse and Fine batches of this sample are identified as A-2C and A-2F respectively.

In the next sample, the total surfactant (plus water) level is reduced to 4 weight percent by utilizing only 1.3 weight percent tristyrylphenol ethoxylate; 0.7 weight percent disodium dodecyl diphenyloxide disulfonate; 0.7 weight percent water; and 1.3 weight percent of the ethoxylated-propoxylated block copolymer. The diethylene glycol is again increased to 31 weight percent to make up the difference. These batches, i.e., the Coarse and Fine batches of this sample are identified as A-3C and A-3F respectively.

The samples are stored at room temperature (24° C.) and 50° C. for four weeks. Syneresis measurements are made at the second, third, and fourth week intervals and the qualitative pourability of the samples determined at the end of the fourth week. The results of these tests are set forth in Table I below.

TABLE I

| Sample | Concentration | Syneresis 2 Weeks | 3 Weeks | 4 Weeks | Pourability 4 Weeks |
|---|---|---|---|---|---|
| | | Room Temperature Coarse | | | |
| A-1C | 10% | 18.2 | 23.4 | 23.4 | difficult |
| A-2C | 7% | 25.3 | 17.4 | 17.4 | easy |
| A-3C | 4% | 13.4 | 16.7 | 16.7 | easy |

TABLE I-continued

| Sample | Concentration | Syneresis 2 Weeks | 3 Weeks | 4 Weeks | Pourability 4 Weeks |
|---|---|---|---|---|---|
| Room Temperature Fine | | | | | |
| A-1F | 10% | 6.7 | 6.7 | 8.5 | difficult |
| A-2F | 7% | 6.2 | 8.3 | 9.2 | mod-difficult |
| A-3F | 4% | 7.4 | 5.6 | 14.5 | slightly-difficult |
| 50° C. Coarse | | | | | |
| A-1C | 10% | 12.9 | 21.0 | 24.6 | mod-difficult |
| A-2C | 7% | 4.6 | 9.4 | 4.8 | mod-difficult |
| A-3C | 4% | 5.8 | 7.8 | 1.5 | slightly-difficult |
| 50° C. Fine | | | | | |
| A-1F | 10% | 4.5 | 6.7 | 6.7 | difficult |
| A-2F | 7% | 0.0 | 4.0 | 1.0 | difficult |
| A-3F | 4% | 0.0 | 2.0 | 4.2 | easy |

The above results demonstrate the outstanding syneresis control achieved via the use of the teachings of the instant invention. Even under long term storage conditions at both high and room temperature conditions, a very concentrated water soluble solid suspension (65% $KNO_3$) can be pourable and continue to exhibit extremely low syneresis.

EXAMPLES 2–9

A number of A-1F type samples are prepared as in Example 1, i.e., having a 10 weight percent surfactant system (plus water) using the same surfactants as in A-1F wherein the weight percent ratios among the surfactants are varied. Syneresis results are obtained 24 hours after the initial preparation. The viscosity measurements are also taken after 24 hours and after the suspension had been stirred thoroughly until no obvious syneresis layer remained. The results of the above-described room temperature tests are set forth in Table II below.

TABLE II

Twenty-Four Hour Evaluations

| Samples | BSU:DSB:F88 Weight % | Syneresis (%) | Viscosity (cps) |
|---|---|---|---|
| A | 3.3:3.3:3.3 | 2.7 | 12406 |
| B | 3.3:2.2:4.4 | 0.0 | 12858 |
| C | 1.0:3.0:6.0 | 4.1 | 15472 |
| D | 3.0:1.0:6.0 | 0.0 | 76831 |
| E | 2.0:4.0:4.0 | 1.3 | 17397 |
| F | 5.0:1.0:4.0 | 0.0 | 51237 |
| G | 5.0:2.0:3.0 | 1.5 | 14175 |
| H | 4.0:2.0:4.0 | 0.0 | 9831 |

With the exception of samples D and F which exhibit unacceptably high initial viscosities, all of the samples using the system of the instant invention, demonstrate exceptional stability (syneresis) and initial overall viscosity.

EXAMPLES 10–17

A second series of samples prepared as in Examples 2–9 are subjected to room temperature (24° C.) and 50° C. syneresis evaluations at the end of a two week storage and a four week storage. The results are set forth in Tables III and IV below.

TABLE III

Two Week Storage Evaluation

| Samples | BSU:DSB:F88 Weight % | RT Syneresis (%) | 50° Syneresis (%) |
|---|---|---|---|
| A | 3.3:3.3:3.3 | 6.1 | 5.6 |
| B | 3.3:2.2:4.4 | 0.0 | 0.8 |
| C | 1.0:3.0:6.0 | 6.1 | 7.0 |
| D | 3.0:1.0:6.0 | 0.0 | 0.0 |
| E | 2.0:4.0:4.0 | 5.4 | 5.3 |
| F | 5.0:1.0:4.0 | 0.0 | 0.0 |
| G | 5.0:2.0:3.0 | 3.7 | 0.8 |
| H | 4.0:2.0:4.0 | 4.7 | 1.3 |

TABLE IV

Four Week Storage Evaluation

| Samples | BSU:DSB:F88 Weight % | RT Syneresis (%) | 50° Syneresis (%) |
|---|---|---|---|
| A | 3.3:3.3:3.3 | 6.2 | 2.9 |
| B | 3.3:2.2:4.4 | 0.0 | 0.0 |
| C | 1.0:3.0:6.0 | 8.3 | 7.7 |
| D | 3.0:1.0:6.0 | 0.0 | 0.0 |
| E | 2.0:4.0:4.0 | 0.9 | 4.3 |
| F | 5.0:1.0:4.0 | 0.0 | 0.0 |
| G | 5.0:2.0:3.0 | 3.9 | 1.5 |
| H | 4.0:2.0:4.0 | 3.7 | 1.5 |

The above results again illustrate the outstanding syneresis results obtainable utilizing the systems of the instant invention.

EXAMPLES 18–25

A third series of samples prepared as in Examples 2–9 are subjected to a Heliopath viscosity evaluation after storage at room temperature (24° C.) for two weeks. The results are depicted in FIG. 1.

As previously indicated by the initial overall viscosity levels, samples D and F have unacceptably high viscosity levels just below the surface of the concentrate after two weeks storage at room temperature. Sample G also shows a large viscosity increase with depth which suggests that significant settling of the suspension is occurring also. However, the balance of the samples show the relative uniformity with depth that can be achieved using the teachings of the instant invention.

EXAMPLES 26–33

The following samples are prepared in accordance with the procedures of Example 1 with i) ammonium dihydrogen phosphate (($NH_4$)$H_2PO_4$) as the water-soluble solid in lieu of the potassium nitrate and ii) propylene glycol in lieu of the diethylene glycol. Other ingredients in their respective weight percentages (all based on the total concentrate weight percent) are as indicated in Table V below.

TABLE V

|  | 26 | 27 | 28* | 29** | 30 | 31 | 32 | 33 |
|---|---|---|---|---|---|---|---|---|
| ($NH_4$) $PO_4$ | 50 | 50 | 50 | 50 | 50 | 50 | 50 | 50 |
| Propylene Glycol | 44 | 44 | 44 | 44 | 44 | 45.9 | 45.5 | 44 |
| Antarox F-88 | 2 | 2 | — | — | 2 | — | — | — |
| Viscosity Improver | | | | | | | | |
| Rhodacal DSB | 2 | — | 2 | 2 | 2 | 2 | 2 | — |

TABLE V-continued

|  | 26 | 27 | 28* | 29** | 30 | 31 | 32 | 33 |
|---|---|---|---|---|---|---|---|---|
| Disulf. Soprophor BSU Styr. | 2 | 2 | 2 | 2 | — | 2 | 2 | — |
| Alipal CO 436 (Nonylphenol (4EO) Ammonium Sulfate) | — | 2 | — | — | — | — | — | 2 |
| Antarox F-108*** | — | — | 2 | 2 | — | — | — | — |
| Igepal DM-710 (Dinonyl (7 EO) Phenol) | — | — | — | — | 2 | — | — | 2 |
| Colloid 245D (Polyacrylic Sodium Salt - Molecular Weight 4500) | — | — | — | — | — | 0.1 | 0.5 | 2 |

*Coarse Grind
**Fine Grind
***Ethoxylated-Propoxylated (128 EO 54 PO 128 EO) Block Copolymer Room temperature syneresis and viscosity measurements are made on each of the samples at 24 hours and 3 weeks storage. Bostwick pourability tests are conducted at the end of the 3 week storage tests. The results are reported in Table VI.

TABLE VI

R. T. Storage Results for Ammonium Di H Phosphate

|  | Syneresis (%) 24 hr./3 wks. | Viscosity (cp) 24 hr./3 wks. | Bostwick Pourability (sec) 3 Weeks |
|---|---|---|---|
| Examples |  |  |  |
| 26 | 3.3/12.5 | 3739/1698 | 16 |
| 27 | 8.1/12.7 | 1844/1540 | 3.5 |
| 28 | 4.5/10.5 | 3513/2487 | 7 |
| 29 | 0.0/3.4 | 8916/5047 | Stopped |
| 30 | 3.0/8.8 | 3833/2006 | 8 |
| 31 | 17.7/28.1 | 230/346 | 2.5 |
| 32 | 6.3/19.6 | 2579/1774 | 7 |
| 33 | 4.0/15.7 | 3661/3783 | 46 |
| Comparisons |  |  |  |
| A-1F | — | — | Stopped |
| A-2F | — | — | Stopped |
| A-3F | — | — | 4 |

Heliopath vertical viscosity profiles at room temperature (24° C.) are also determined at 3 weeks on similarly prepared samples of Examples 26 through 33 and the results are presented in FIG. 2.

It can be observed from FIG. 2 (and FIG. 1) that one can quite easily determine if compacting or settling is occurring in a suspension via a Heliopath viscosity profile. With the exception of Samples 32A and 33A, the viscosities throughout the depth of the highly concentrated suspensions of this invention, are remarkably uniform.

Other applications of this invention, where a product is required in the form of a highly concentrated suspension of water-soluble solids, include concentrates for the production of sprayable agricultural formulations, sodium chloride slurries for road de-icing, the bulk delivery by pipeline or inorganic salts, as well as the transportation of slurry explosive compositions.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A nonaqueous suspension concentrate comprising:
   a) from 40 to 85 weight percent of a compound having a solubility in water of greater than one percent based on the weight of said compound and water at 24° C., the particles of which in said concentrate having a volume average diameter of from 0.5 microns to 500 microns;
   b) from 11 to 58 weight percent of a water miscible, organic liquid carrier;
   c) from 4 to 15 weight percent of a surfactant system comprising:
      i) from 2 to 7 weight percent of a nonionic polymeric viscosity improver;
      ii) from 1 to 7 weight percent of an anionic surfactant; and
      iii) from 1 to 7 weight percent of a bulky nonionic surfactant of the formula $R_6-O-(C_nH_{2n}O)_x-R_7$ wherein $R_6$ is selected from the group consisting of a phenyl; a mono-, di- or tri-substituted phenyl; a phenyl $C_1-C_6$ alkyl; and a mono-, di-, or tri-substituted phenyl $C_1-C_6$ alkyl wherein the phenyl substituent group(s) each have a total of 1 to 30 carbon atoms, and wherein each substitution can be a saturated or unsaturated straight or branched carbon chain, a phenyl, an alkyl phenyl, a phenyl alkyl, or an alkyl phenyl alkyl group; wherein n is from 2 to 4 and may be the same or different for each alkylene oxide unit; wherein $R_7$ is a hydrogen, phosphate or sulfate entity; and wherein x is from 2 to 100; and
   d) from 0 to 30 weight percent water;
with the proviso that the suspension concentrate properties at 24° C. are within the stabilization zone limitations of:
   1) an initial Brookfield viscosity of from 100 to 30,000 cps;
   2) a Heliopath viscosity of less than 400,000 cps at two weeks after initial preparation and two inches below the surface of the concentrate;
   3) a Bostwick Consistometer 10 cm time equal to or less than one minute; and
   4) syneresis at 24 hours of less than 30% with less than 5% after thirty inversions;
all of the above weight percents being based on the total weight of the concentrate except where indicated.

2. The nonaqueous suspension concentrate of claim 1 wherein:
   i) the nonionic polymeric viscosity improver is selected from the group consisting of
      a) polyacrylic acids and the sodium salts thereof;
      b) polyalkylene oxide block copolymers; and
      c) mixtures thereof;
   ii) the anionic surfactant is selected from the group consisting of
      a) alkyl or alkyl ether sulfates of the formulae $R-O-SO_3-M$ or $R-O-(C_2H_4O)_x-SO_3-M$ respectively wherein R is an alkyl, alkenyl or alkylaryl group of about 8 to about 22 carbon atoms, x is 1 to 10, and M is a water-soluble cation;
      b) water-soluble salts of the formula $R_1-SO_3-M$ wherein $R_1$ is selected from the group consisting of
         1) a straight or branched chain, saturated aliphatic hydrocarbon radical having from 8 to 24 carbon atoms;

2) a mono-, di-, or tri- $C_1$–$C_6$ alkyl substituted aryl wherein the aryl is a phenyl or naphthyl group;
3) alpha-olefins having 12 to 24 carbon atoms; and
4) naphthalene-formaldehyde condensation products;
c) isethionates;
d) n-methyl taurates;
e) sulfosuccinates;
f) sulfosuccinamates;
g) B-alkyloxy alkane sulfonates;
h) disulfonates; and
i) mixtures thereof; and iii) the bulky nonionic surfactant comprises at least one poly-oxy ethylenated and/or -oxy propylenated poly (1-phenyl ethyl) phenol or phenyl ester of the formula:

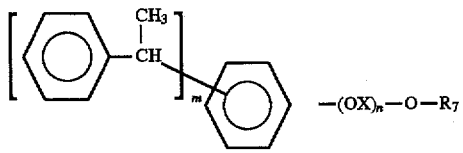

wherein:

m is 2 or 3;

(OX) is a recurring oxy ethylenated and/or oxy propylenated unit;

n is from 12 to 35;

and $R_7$ is a hydrogen, phosphate or sulfate entity.

3. The nonaqueous suspension concentrate of claim 1 wherein the water-miscible, organic liquid carrier is selected from the group consisting of $C_1$–$C_4$ alkanols; $C_1$–$C_4$ alkadiols; and mixtures thereof.

4. The nonaqueous suspension concentrate of claim 3 wherein the carrier is diethylene glycol.

5. A nonaqueous suspension concentrate comprising:

a) from 40 to 85 weight percent of a compound having a solubility in water of greater than one percent based on the weight of said compound and water at 24° C., the particles of which in said concentrate having a volume average diameter of from 0.5 microns to 500 microns;

b) from 11 to 58 weight percent of a water miscible, organic liquid carrier;

c) from 4 to 15 weight percent of a surfactant system comprising:
  i) from 2 to 7 weight percent of an ethoxylated-propoxylated block copolymer;
  ii) from 1 to 7 weight percent of disodium dodecyl diphenyloxide disulfonate; and
  iii) from 1 to 7 weight percent of tristyrylphenol (16) ethoxylate; and d) from 0 to 30 weight percent water; with the proviso that the suspension concentrate properties at 24° C. are within the stabilization zone limitations of:
  1) an initial Brookfield viscosity of from 100 to 30,000 cps;
  2) a Heliopath viscosity of less than 400,000 cps at two weeks after initial preparation and two inches below the surface of the concentrate;
  3) a Bostwick Consistometer 10 cm time equal to or less than one minute; and
  4) syneresis at 24 hours of less than 30% with less than 5% after thirty inversions;

all of the above weight percents being based on the total weight of the concentrate except where indicated.

* * * * *